United States Patent
Kage (10) Patent No.: US 10,928,394 B2
(45) Date of Patent: Feb. 23, 2021

(54) RAPID TEST FOR LYME BACTERIA

(71) Applicant: Julian R. K. Kage, Glastonbury, CT (US)

(72) Inventor: Julian R. K. Kage, Glastonbury, CT (US)

(*) Notice: Subject to any disclaimer, the term of this patent is extended or adjusted under 35 U.S.C. 154(b) by 0 days.

(21) Appl. No.: 16/422,802

(22) Filed: May 24, 2019

(65) Prior Publication Data

US 2020/0256870 A1    Aug. 13, 2020

Related U.S. Application Data (60) Provisional application No. 62/802,547, filed on Feb. 7, 2019.

(51) Int. Cl.
*G01N 33/569* (2006.01)
*G01N 33/543* (2006.01)

(52) U.S. Cl.
CPC . *G01N 33/56911* (2013.01); *G01N 33/54386* (2013.01)

(58) Field of Classification Search
None
See application file for complete search history.

(56) References Cited

U.S. PATENT DOCUMENTS

| | | | |
|---|---|---|---|
| 9,201,071 B2 | 12/2015 | Mehra et al. | |
| 2009/0246886 A1* | 10/2009 | Buck | G01N 33/558 436/501 |
| 2010/0015634 A1 | 1/2010 | VanDine et al. | |
| 2016/0223536 A1 | 8/2016 | Johnson et al. | |

OTHER PUBLICATIONS

2015 Reported Lyme Cases—Top 15 States, https://LymeDiseaseAssociation.org/about-lyme/cases-stats-maps-a-graphs/2015-reported-lyme-cases-top-15-states/?print=pdf, 2015 (1 page).
CDC, "Lyme Disease Maps: Historical Data—Reported Cases of Lyme Disease—United States, 2017", https://www.cdc.gov/lyme/stats/maps.html, last reviewed, Feb. 19, 2019 (1 page).
CDC, "Lyme Disease", Centers for Disease Control and Prevention, http://www.cdc.gov/lyme/index.html, accessed Jan. 19, 2018 (161 pages).
CDC, "Tickborne Diseases of the United States: A Reference Manual for Healthcare Providers", Fifth Edition, https://www.cdc.gov/ticks/tickbornediseases/TickborneDiseases-P.pdf, 2018 (52 pages).
Lateral Flow Assay Architecture, US National Aeronautics and Space Administration, http://exploration.nasa.gov/articles/images/homeplanet_3.jpg, Mar. 20, 2007 (6 pages).
Lyme Disease Funding, Treatment Guidelines, Symptoms, https://lymediseaseassociation.org/?start=45, 2019 (8 pages).
Lyme Disease in the US, Total new cases reported from 2003-2012, Center for Disease Control and Prevention, http://www.cdc.gov/lyme/stats/index.html (1 page).
Lyme Disease Symptoms, Early Lyme vs Chronic Lyme, Lymedisease.org, http://tinyurl.com/kfvu8yt, 2014 (1 page).
Lyme Disease Symptoms, https://www.lymedisease.org/lyme-basics/lyme-disease/symptoms/, 2018 (5 pages).
Lyme Disease, Connecticut State Department of Public Health, https://portal.ct.gov/DPH/Epidemiology-and-Emerging-Infections/Lyme-Disease-Signs--Symptoms, Jul. 1, 2019 (14 pages).
Lyme Prevalence 2017 Forecast, "New Lyme disease forecast map targets rising tide of ticks", https://www.lymedisease.org/clemson-tick-map/, LymeDisease.org, May 12, 2017 (12 pages).
Wong, R.C. et al., "Lateral Flow Immunoassay", Humana Press, Springer, New York, NY, 2009 (223 pages).
World Health Organization, "Vector-borne diseases", https://www.who.int/news-room/fact-sheets/detail/vector-borne-diseases, Oct. 31, 2017 (4 pages).
International Search Report and Written Opinion issued by the U.S. Patent and Trademark Office in International Application No. PCT/US2020/16960, dated Apr. 30, 2020 (7 pages).

* cited by examiner

*Primary Examiner* — Mary Maille Lyons
(74) *Attorney, Agent, or Firm* — Wilmer Cutler Pickering Hale and Dorr LLP (57) ABSTRACT

The subject matter disclosed herein provides a method and a device for detection of one or more bacteria in a sample.

1 Claim, 5 Drawing Sheets

Specification includes a Sequence Listing.

FIG. 5 ized sample solution to occur along an elongated nitrocellulose
RAPID TEST FOR LYME BACTERIA This application claims the benefit of and priority under 35 U.S.C. § 119(e) to U.S. Ser. No. 62/802,547 filed Feb. 7, 2019, the contents of which is hereby incorporated by reference in its entirety.

All patents, patent applications and publications cited herein are hereby incorporated by reference in their entirety. The disclosures of these publications in their entireties are hereby incorporated by reference into this application.

This patent disclosure contains material that is subject to copyright protection. The copyright owner has no objection to the facsimile reproduction by anyone of the patent document or the patent disclosure as it appears in the U.S. Patent and Trademark Office patent file or records, but otherwise reserves any and all copyright rights.

SEQUENCE LISTING

The instant application contains a Sequence Listing which has been submitted electronically in ASCII format and is hereby incorporated by reference in its entirety. Said ASCII copy, created on Jul. 28, 2020, is named 2215284_124US2_SL.txt and is 624 bytes in size.

BACKGROUND OF THE INVENTION

Lyme disease, also known as Borreliosis is a debilitating condition caused by the bacterium *Borrelia burgdorferi* transmitted by the Deer tick (also known as the Blacklegged Tick). The Deer tick may contain among other parasites, viruses and bacteria, a bacterium called *Borrelia burgdorferi*, which causes Lyme disease. Ticks can get infected with *Borrelia burgdorferi* from the white footed mouse, although ticks are not known to get sick from the infections. Only female Deer ticks can pass on Lyme disease due to the fact that only females feed on blood, which can allow for the bacterial infection to spread. The majority of tick bites that result in *Borrelia burgdorferi* infection and Lyme are caused by Nymphs, immature ticks that are less than 2 mm in size. Nymphs feed predominantly during the spring and summer months which often coincides with an increase in tick bites reported. A tick can attach itself to any part of the human body, although they are most commonly found in warm areas such as behind the ear lobes or armpits. When a tick attaches onto a human body it transmits the *Borrelia burgdorferi* bacterium into the bloodstream of the host. According to the Centers for Disease Control (CDC), a tick must be attached for 36 to 48 hours before it transmits Lyme disease.

Symptoms of Lyme disease include an infection related bulls-eye rash referred to as erythema migrans, pains and swelling of the joints, as well as fever and fatigue. An accurate and early detection of Lyme disease is critical to effective treatment. Erythema migrans, the most distinctive symptom and reliable way of clinically diagnosing Lyme disease, is only present early during the infection cycle and may not appear in all infected individuals. Other clinical symptoms that have been associated with Lyme disease, such as Bell's palsy, are not specific enough to determine early clinical diagnosis in the absence of erythema migrans.

Antibiotic treatment for Lyme disease is very effective. Only about half of Deer ticks are carriers of *Borrelia*. Treatment for Lyme disease should be started as soon as possible after a tick bite, but unnecessary treatment with antibiotics can cause significant problems such as induction of resistance of common gut bacteria and allergic reactions. Current tests for identification of *Borrelia*-carrying ticks are very time consuming.

Accordingly, there remains a need in the art for rapid and specific assays for detecting *Borrelia burgdorferi* antigens in ticks in order to be able to treat only patients that have been bitten by a carrier tick.

SUMMARY OF THE INVENTION

In certain aspects, the invention provides a method for detecting one or more vectors in a sample comprising homogenizing a sample on a sample pad, applying biotinylated analogue protein, streptavidin-gold, and flow buffer to homogenized sample to obtain homogenized sample solution, allowing for capillary flow of said homogenized sample solution to occur along an elongated nitrocellulose strip contacting at a first short edge said sample pad, allowing homogenized sample solution to contact a first read-out line on the nitrocellulose strip and a second read-out line on the nitrocellulose strip, wherein first read-out line comprises at least one vector-specific antibody, further wherein second read-out line comprises biotinylated albumin and collecting excess sample in cellulose wick contacting a second short edge of said nitrocellulose strip.

In certain aspects, the inventions provides a device for detecting one or more vectors in a sample comprising a holder with a top part comprising at least one sample opening and at least one observation opening and a continuous bottom part, a top glass slide and a bottom glass slide disposed between the top part and the bottom part of said holder such that the holder encases the top glass slide and the bottom glass slide, at least one sample pad disposed on top of the bottom glass slide such that at least a portion of the at least one sample pad is not covered by the top glass slide and at least a portion of the at least one sample pad is in contact with a first short edge of at least one elongated nitrocellulose strip and at least a portion of the sample pad aligns with at least one sample opening on the top part of the holder, wherein a first portion of said at least one nitrocellulose strip is pre-loaded with at least one vector-specific antibody and a second portion of the at least one nitrocellulose strip is pre-loaded with biotinylated streptavidin, further wherein the at least one nitrocellulose strip is disposed between the top glass slide and the bottom glass slide and at least one cellulose wick disposed in contact with a second short edge of the at least nitrocellulose strip.

BRIEF DESCRIPTION OF FIGURES

The patent or application file contains at least one drawing originally in color.

DETAILED DESCRIPTION OF THE INVENTION

In certain aspects, the invention provides a method for detecting one or more *Borrelia burgdorferi* proteins in a sample comprising homogenizing a sample on a sample pad, applying biotinylated analogue protein, streptavidin-gold, and flow buffer to homogenized sample to obtain homogenized sample solution, allowing for capillary flow of said homogenized sample solution to occur along an elongated nitrocellulose strip contacting at a first short edge said sample pad, allowing homogenized sample solution to contact a first read-out line on the nitrocellulose strip and a second read-out line on the nitrocellulose strip, wherein first read-out line comprises at least one *Borrelia burgdorferi* protein-specific antibody, further wherein second read-out line comprises biotinylated albumin and collecting excess sample in cellulose wick contacting a second short edge of said nitrocellulose strip.

In certain aspects, the inventions provides a device for detecting one or more *Borrelia burgdorferi* proteins in a sample comprising a holder with a top part comprising at least one sample opening and at least one observation opening and a continuous bottom part, a top glass slide and a bottom glass slide disposed between the top part and the bottom part of said holder such that the holder encases the top glass slide and the bottom glass slide, at least one sample pad disposed on top of the bottom glass slide such that at least a portion of the at least one sample pad is not covered by the top glass slide and at least a portion of the at least one sample pad is in contact with a first short edge of at least one elongated nitrocellulose strip and at least a portion of the sample pad aligns with at least one sample opening on the top part of the holder, wherein a first portion of said at least one nitrocellulose strip is pre-loaded with at least one *Borrelia burgdorferi* protein-specific antibody and a second portion of the at least one nitrocellulose strip is pre-loaded with biotinylated streptavidin, further wherein the at least one nitrocellulose strip is disposed between the top glass slide and the bottom glass slide and at least one cellulose wick disposed in contact with a second short edge of the at least nitrocellulose strip.

Lyme disease is an extremely harmful and painful disease that can be easily treated with antibiotics. However, as with all medication there can be undesired side-effects. Additionally, it is not recommended that medication be taken unless absolutely necessary. Therefore, when experiencing a tick bite, it is important to know if the tick carries Lyme disease, which can be transmitted to human subjects. The subject matter disclosed herein provides a method for rapid and robust detection of Lyme disease-associated bacteria in ticks. This can inform a medical professional as to possible course of treatment.

Lateral Flow Immunoassay

Figure 1:
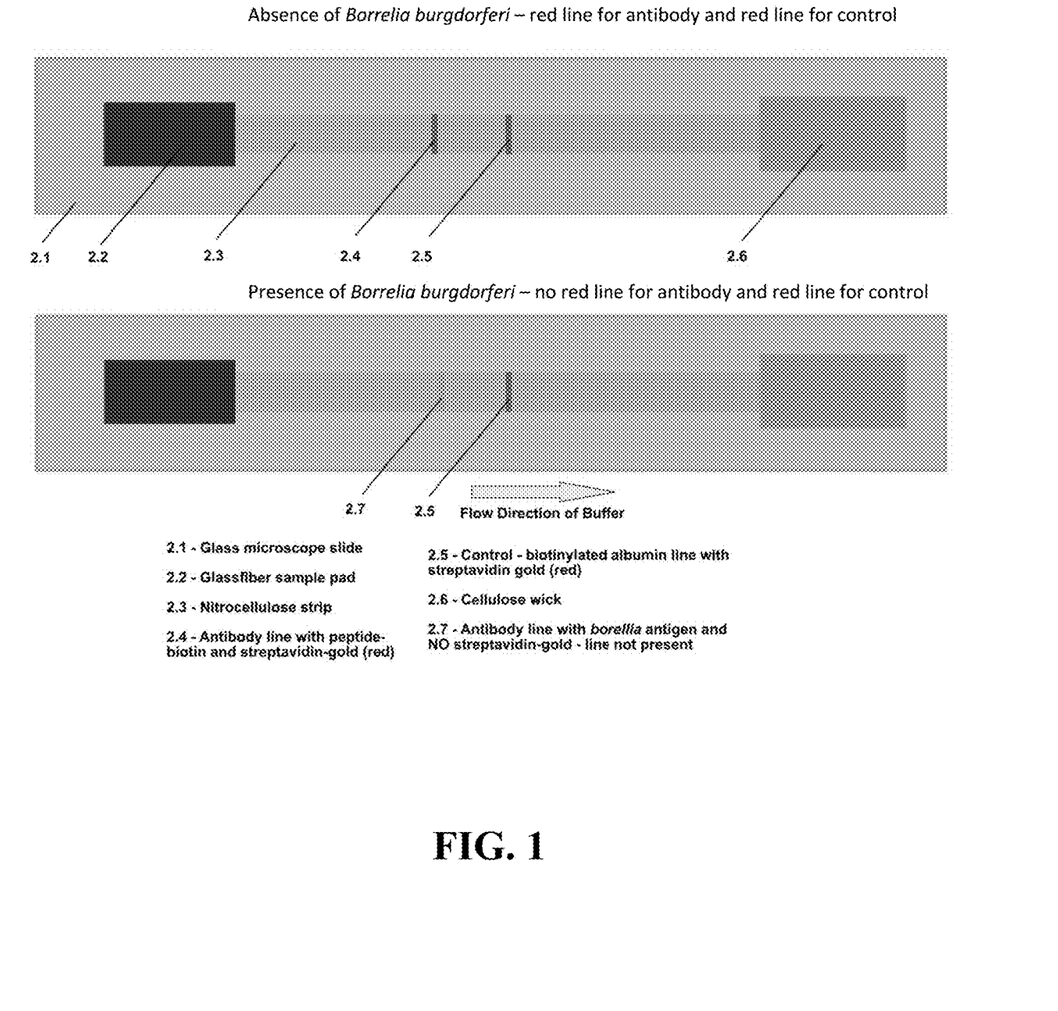
FIG. 1 shows a diagram of a lateral flow immunoassay.

Lateral Flow Immunoassay is a simple and cost-effective methodology for detecting a target protein in a liquid sample. Tests based on this methodology can be used at a point of care center or for at-home testing. The technology incorporates a series of capillary beds, which have the capacity to transport fluids spontaneously. FIG. 1 shows a lateral flow immunoassay device positioned on a glass microscope slide (2.1). The device can include capillary beds consisting of glass fiber, nitrocellulose, or cellulose. Capillary beds take advantage of the capillary action displayed by liquids, which is the ability of liquids to flow through narrow spaces even in opposition to external forces. Capillary action can be observed in the drawing up of liquids into materials such as fibers or cellulose. It occurs due to intermolecular forces between the liquid and surrounding solid surfaces. If the diameter of the space is sufficiently small, then the combination of surface tension of the liquid and the adhesive forces between the liquid and the surrounding solid surface act to propel the liquid into the narrow space. A glass fiber sample pad (2.2) can be the first element in the capillary bed series and may hold any excess fluid from a sample applied on it. The sample can migrate in a unidirectional flow from the sample pad (2.2) along a nitrocellulose strip (2.3) as shown in FIG. 1. In the course of capillary flow, the sample can come into contact with one or more read-out lines. FIG. 1 exemplifies two read-out lines, a test line (2.4), which can be pre-loaded with an antibody specifically recognizing an antigen of interest, and a control line (2.5), which can be pre-loaded with biotinylated albumin with the capacity to specifically bind streptavidin-gold. The control line (2.5) can change color when streptavidin-gold comes in contact with the pre-loaded biotinylated albumin, indicating that the testing is proceeding under favorable conditions for reliable results. The test line (2.4) can change color only in the presence of *Borrelia burgdorferi*-specific biotinylated peptide, indicating the absence of the bacteria in the sample. As shown in FIG. 1 test line (2.7) may not change color indicating presence of *Borrelia burgdorferi* from sample, as *Borrelia* competes with the biotinylated *Borrelia* peptide. After migrating along the nitrocellulose strip (2.3) and passing through the read-out lines (2.4; 2.4; 2.7), the sample enters the final porous material of the series, the cellulose wick (2.6), which functions as a waste container as shown in FIG. 1.

There are two main types of lateral flow immunoassays. A "sandwich assay" and a "competitive assay". In a "sandwich assay", a migrating sample first encounters a conjugated antibody, which can be labelled with an antibody specific to the target protein. If the target protein is present in the sample, the conjugated antibody can bind to it and subsequently reach the test line. The test line may also contain antibodies specific to the target protein and will change color upon reaction with target protein. Thus, the target protein is "sandwiched" between two antibodies. In "competitive assays", the target protein has to compete with an added analogue in the sample in order to bind specific antibodies on the test line. In competitive assays, a non-labelled target protein in a sample, such as a homogenized tick sample, competes with labelled proteins to bind an antibody. This type of assay also uses a color change of the test line as a read-out.

The subject matter disclosed herein relates to detection of an antigen such as the bacterium *Borrelia burgdorferi* in a sample using a competitive lateral flow immunoassay. In some embodiments, the antigen can be a *Borrelia burgdorferi* protein or an analogue thereof. In some embodiments, the antigen can be the VisE protein, the antigenic variation protein of *Borrelia burgdorferi*. In some embodiments, the antigen can be a C6 peptide. In some embodiments, the C6 peptide reproduces a sequence of the invariable region 6 of the VisE protein. In some embodiments, the C6 peptide is a synthetic peptide of a single 25 amino acid sequence of the *Borrelia burgdorferi* VisE protein. The C6 peptide can be used with a high degree of sensitivity as a test antigen in a lateral flow immunoassay. In some embodiments, the sample includes one or more homogenized ticks. In some embodiments, the sample includes one or more tick-associated proteins.

QuickLyme Test

The subject matter disclosed herein relates to a test for detection of Lyme bacteria (*Borrelia burgdorferi*) in a sample (hereafter referred to as "QuickLyme" test). In some embodiments, the sample can be one or more ticks. In some embodiments, the sample can include isolated VisE protein or an analogue thereof. In some embodiments, the sample can include C6 peptide. In some embodiments, the sample can include another short synthetic sequence peptide of *Borrelia*, which is biotinylated. In some embodiments, one or more ticks can be placed onto the sample pad in one end of the QuickLyme nitrocellulose strip and homogenized. To aid in capillary flow and detection of tick proteins, about 3 to about 5 drops of C6 peptide solution, about 3-5 drops of streptavidin-gold solution, and about 3 to about 5 drops of flow buffer can be added to the homogenized sample or one or more ticks to obtain a homogenized sample solution or tick-associated proteins. In some embodiments, the flow buffer consists of Phosphate Buffered Saline, which can keep pH levels stable in the sample during flow. Capillary forces pull the applied sample and liquids across a nitrocellulose strip.

Figure 2:
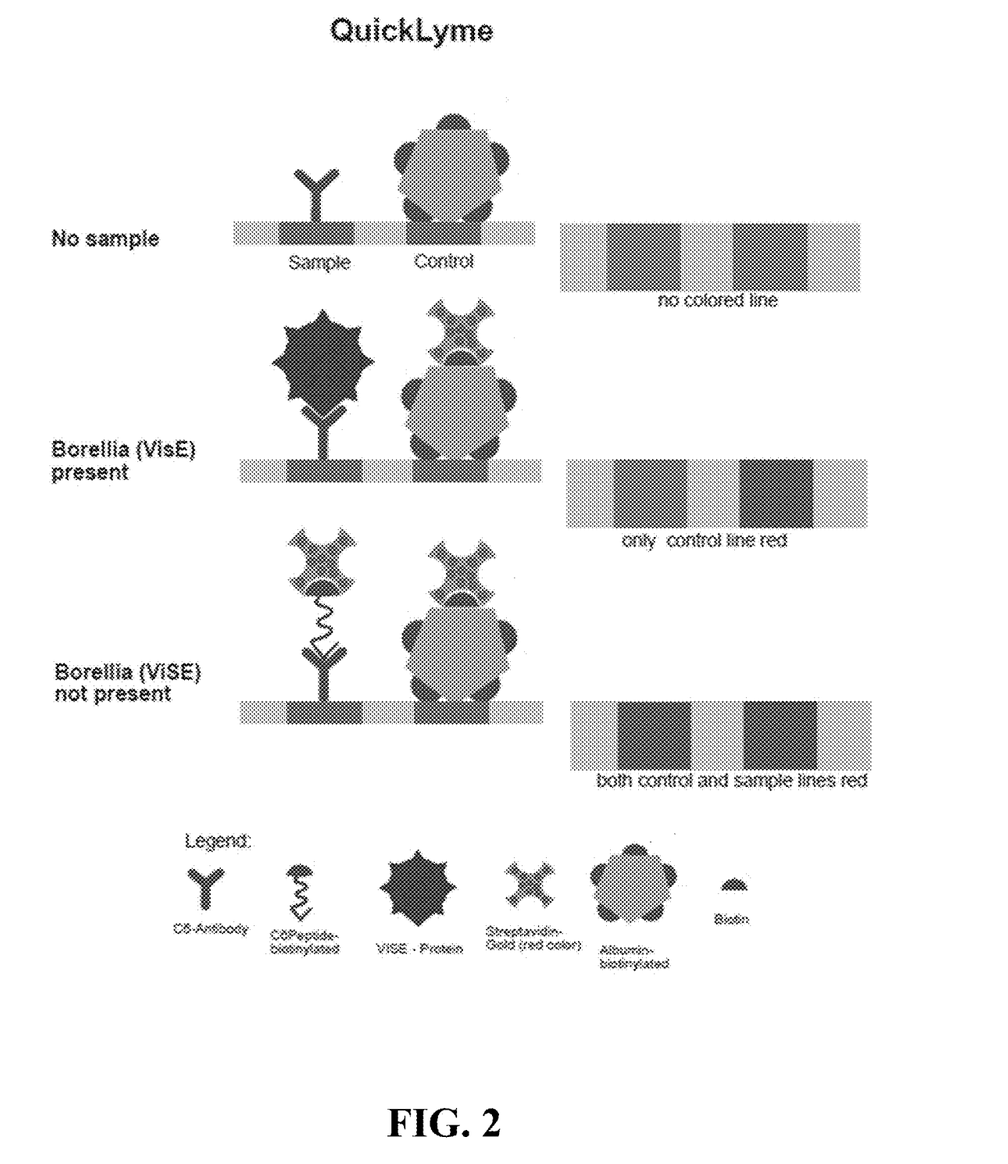
FIG. 2 shows a diagram of an assay for the detection of *Borrelia burgdorferi*.

FIG. 2 shows a diagram of the protein components, which can be incorporated into a QuickLyme test for detecting the presence of *Borrelia burgdorferi* in a sample. As shown in FIG. 2, an antibody specific to the biotinylated C6 protein can be pre-loaded onto a test (sample) line of a nitrocellulose strip. In some embodiments, the antibody pre-loaded onto the test line can be specific for the VisE protein. In some embodiments, the antibody pre-loaded onto the test line can be specific for another *Borrelia burgdorferi* protein or complex of proteins. In some embodiments, the antibody pre-loaded onto the test line can be specific for one or more proteins associated with bacterium other than *Borrelia burgdorferi*. As shown in FIG. 2, the control line can be pre-loaded with biotinylated albumin particles. When biotinylated albumin comes in contact with streptavidin-gold solution in the sample, the control line can become colored as a result of a binding reaction between streptavidin and biotin. In some embodiments, the control line can become red in color. In the example shown in FIG. 2, when VisE protein is present in the sample, it specifically binds to the anti-VisE/C6 antibody in the test line and there is no color change observed because there is no color particle attached to the VisE protein, which is a proxy for *Borrelia burgdorferi* in the sample. Thus, when the QuickLyme test only presents with one colored line (the control read-out line), it is indicative of presence of VisE protein in the sample and possibly a *Borrelia burgdorferi* infection in tick sample as exemplified in FIG. 2. The biotinylated C6 peptide added to the sample can facilitate binding of streptavidin-gold to the anti-C6 antibody and indicate absence of VisE protein, and thus absence of *Borrelia burgdorferi*, from the tick sample. In the example of FIG. 2, when the test and control read-out line become red, it is indicative of a negative test for VisE protein and *Borrelia burgdorferi* infection. The example in FIG. 2 shows a "competitive assay" because if VisE protein is present in the sample, it can compete with the added C6 peptide for biding to the specific antibody.

In some embodiments, it is important to avoid drying up of sample by timely adding reactants to sample pad.

Arthropods

Arthropods are invertebrates with segmented bodies and jointed limbs. Their exoskeleton or cuticles consist of chitin, a polymer of glucosamine. Estimates of the number of arthropod species vary between 1,170,000 and 5 to 10 million and account for over 80 percent of all known living animal species. Medically, arthropods are more significant as carriers of diseases such as malaria, yellow fever, dengue fever, and elephantiasis (via mosquitoes), African sleeping sickness (via tsetse flies), typhus fever (via lice), bubonic plague (via fleas), and Rocky Mountain spotted fever and Lyme disease (via ticks). Many diseases of domesticated animals are also transmitted by arthropods.

In one embodiment, the subject matter disclosed herein relates to a method for detecting bacteria in a sample of one or more arthropods. In one embodiment, the subject matter disclosed herein relates to a lateral flow immunoassay device for detecting an antigen in a sample of one or more arthropods. In some embodiments, the sample includes a homogenized arthropod. In some embodiments, the sample includes one or more homogenized arthropods. In some embodiments, the sample includes two or more homogenized arthropods from two or more species. In some embodiments, the arthropod is a mosquito. In some embodiments, the arthropod is a tick. In some embodiments, the arthropod is flea. In some embodiments, the arthropod carries a disease-causing antigen.

In some embodiments, the antigen causes malaria. In some embodiments, the antigen causes yellow fever. In some embodiments, the antigen causes dengue fever. In some embodiments, the antigen causes elephantiasis. In some embodiments, the antigen causes African sleeping sickness. In some embodiments, the antigen causes typhus fever. In some embodiments, the antigen causes bubonic plague. In some embodiments, the antigen causes Rocky Mountain spotted fever. In some embodiments, the antigen causes Lyme disease.

Vectors and Vector-Bourne Diseases

Vectors are living organisms that can transmit infectious diseases between humans or from animals to humans. Vector-borne diseases are infections transmitted by the bite of infected arthropod species, such as mosquitoes, ticks, triatomine bugs, sandflies, and blackflies. Arthropod vectors are cold-blooded (ectothermic) and thus especially sensitive to climatic factors. However, climate is only one of many factors influencing vector distribution, such as habitat destruction, land use, pesticide application, and host density. Many vectors are bloodsucking insects, which ingest disease-producing microorganisms during a blood meal from an infected host (human or animal) and later inject it into a new host during their subsequent blood meal. Mosquitoes are the best known disease vector. Others include ticks, flies, sandflies, fleas, triatomine bugs and some freshwater aquatic snails.

Diseases that can be spread by mosquitoes include, but are not limited to, chikungunya, dengue fever, lymphatic filariasis, rift valley fever, yellow fever, zika, malaria, lymphatic filariasis, Japanese encephalitis, Lymphatic filariasis, and West Nile fever. Diseases that can be spread by sandflies include, but are not limited to, leishmaniasis, and sandfly fever (phelebotomus fever). Diseases that can be spread by ticks include, but are not limited to, Crimean-Congo hemorrhagic fever, Lyme disease, relapsing fever (borreliosis), rickettsial diseases (spotted fever and Q fever), tick-borne encephalitis, and tularaemia. Diseases that can be spread by triatomine bugs include, but are not limited to, chagas disease (American trypanosomiasis). Diseases that can be spread by tsetse flies include, but are not limited to, Sleeping sickness (African trypanosomiasis). Diseases that can be spread by fleas include, but are not limited to, plague (transmitted by fleas from rats to humans), and rickettsiosis. Diseases that can be spread by black flies include, but are not limited to, onchocerciasis (river blindness). Diseases that can be spread by aquatic snails include, but are not limited to, schistosomiasis (bilharziasis). Diseases that can be spread by lice include, but are not limited to, typhus and louse-borne relapsing fever.

In one embodiment, the subject matter disclosed herein relates to a method for detecting bacteria in a sample of one or more vectors. In one embodiment, the subject matter disclosed herein relates to a lateral flow immunoassay device for detecting an antigen in a sample of one or more vectors. In some embodiments, the sample includes a homogenized vector. In some embodiments, the sample includes one or more homogenized vectors. In some embodiments, the sample includes two or more homogenized vectors from two or more species. In some embodiments, the vector is a mosquito. In some embodiments, the vector is a tick. In some embodiments, the vector is flea. In some embodiments, the vector carries a disease-causing antigen.

In some embodiments, the antigen causes chikungunya. In some embodiments, the antigen causes dengue fever. In some embodiments, the antigen causes lymphatic filariasis. In some embodiments, the antigen causes rift valley fever. In some embodiments, the antigen causes yellow fever. In some embodiments, the antigen causes zika. In some embodiments, the antigen causes malaria. In some embodiments, the antigen causes lymphatic filariasis. In some embodiments, the antigen causes Japanese encephalitis. In some embodiments, the antigen causes lymphatic filariasis. In some embodiments, the antigen causes West Nile fever. In some embodiments, the antigen causes leishmaniasis. In some embodiments, the antigen causes Crimean-Congo hemorrhagic fever. In some embodiments, the antigen causes Lyme disease. In some embodiments, the antigen causes relapsing fever (borreliosis). In some embodiments, the antigen causes rickettsial diseases (spotted fever and Q fever). In some embodiments, the antigen causes tick-borne encephalitis. In some embodiments, the antigen causes tularaemia. In some embodiments, the antigen causes chagas disease (American trypanosomiasis). In some embodiments, the antigen causes sleeping sickness (African trypanosomiasis). In some embodiments, the antigen causes plague. In some embodiments, the antigen causes rickettsiosis. In some embodiments, the antigen causes onchocerciasis (river blindness). In some embodiments, the antigen causes schistosomiasis (bilharziasis). In some embodiments, the antigen causes typhus. In some embodiments, the antigen causes louse-borne relapsing fever.

Antigens

In one embodiment, a homogenized sample can include one or more of the following antigens:
 Bacterium that causes Anaplasmosis
 Parasite that causes Babesiosis
 Bacterium that causes *Borrelia mayonii*
 Bacterium that causes *Borrelia miyamotoi*
 Bacterium that causes Bourbon virus
 Virus that causes Colorado tick fever (CTF)
 Bacterium that causes Ehrlichiosis
 Virus that causes Heartland virus
 Bacterium that causes Lyme disease
 Virus that causes Powassan virus disease
 Bacterium that causes *Rickettsia parkeri rickettsiosis*
 Bacterium that causes Rocky Mountain spotted fever (RMSF)
 Bacterium that causes START (Southern tick-associated rash illness)
 Bacterium that causes Tickborne relapsing fever (TBRE)
 Bacterium that causes Tularemia
 Bacterium that causes 364D ricketsiosis
 Bacterium that causes Crimean-Congo hemorrhagic fever
 Bacterium that causes Imported tickborne spotted fevers
 Bacterium that causes Kyasanur forest disease
 Most types of *Borrelia*
 Bacterium that causes Omsk Hemorrhagic Fever (OHF)
 Bacterium that causes Tickborne encephalitis (TBE)
 Bacterium that causes African tick bite fever (ATBF)

In one embodiment, the subject matter disclosed herein is a method for detecting the presence of one or more of the following antigens in a sample:
 Bacterium that causes Anaplasmosis
 Parasite that causes Babesiosis
 Bacterium that causes *Borrelia mayonii*
 Bacterium that causes *Borrelia miyamotoi*
 Bacterium that causes Bourbon virus
 Virus that causes Colorado tick fever (CTF)
 Bacterium that causes Ehrlichiosis
 Virus that causes Heartland virus
 Bacterium that causes Lyme disease
 Virus that causes Powassan virus disease
 Bacterium that causes *Rickettsia parkeri rickettsiosis*
 Bacterium that causes Rocky Mountain spotted fever (RMSF)
 Bacterium that causes START (Southern tick-associated rash illness)
 Bacterium that causes Tickborne relapsing fever (TBRE)
 Bacterium that causes Tularemia
 Bacterium that causes 364D ricketsiosis
 Bacterium that causes Crimean-Congo hemorrhagic fever
 Bacterium that causes Imported tickborne spotted fevers
 Bacterium that causes Kyasanur forest disease
 Most types of *Borrelia*
 Bacterium that causes Omsk Hemorrhagic Fever (OHF)
 Bacterium that causes Tickborne encephalitis (TBE)
 Bacterium that causes African tick bite fever (ATBF)

In one embodiment, the subject matter disclosed herein is a device for detecting the presence one or more of the following antigens in a sample:
 Bacterium that causes Anaplasmosis
 Parasite that causes Babesiosis
 Bacterium that causes *Borrelia mayonii*
 Bacterium that causes *Borrelia miyamotoi*
 Bacterium that causes Bourbon virus
 Virus that causes Colorado tick fever (CTF)
 Bacterium that causes Ehrlichiosis
 Virus that causes Heartland virus
 Bacterium that causes Lyme disease
 Virus that causes Powassan virus disease Bacterium that causes *Rickettsia parkeri rickettsiosis*
Bacterium that causes Rocky Mountain spotted fever (RMSF)
Bacterium that causes START (Southern tick-associated rash illness)
Bacterium that causes Tickborne relapsing fever (TBRE)
Bacterium that causes Tularemia
Bacterium that causes 364D ricketsiosis
Bacterium that causes Crimean-Congo hemorrhagic fever
Bacterium that causes Imported tickborne spotted fevers
Bacterium that causes Kyasanur forest disease
Most types of *Borrelia*
Bacterium that causes Omsk Hemorrhagic Fever (OHF)
Bacterium that causes Tickborne encephalitis (TBE)
Bacterium that causes African tick bite fever (ATBF)

EXAMPLES

Example 1

In the U.S., the New England region as well as areas of the Pacific Coast are known to house large numbers of Deer ticks, also known as the blacklegged tick. Lyme disease can be extremely painful and although rare, the Centers for Disease Control and Prevention (CDC) has had 36 reported deaths from Lyme disease. Because of this, it is extremely important that there is a rapid method of early detection of ticks carrying the *Borrelia* bacteria. The State of Connecticut offers free tick tests, however, results can take two weeks or more.

The QuickLyme test is a faster, cheaper, and reliable way to test for detecting bacterial antigens in ticks that only takes a few minutes and there is no need to send specimens to a laboratory or be supervised by a medical professional. The test can consist of a nitrocellulose strip with a sample pad on one side, and a wick on the opposite end of the nitrocellulose strip. In one embodiment, the sample is a synthetic protein with the same structure as that of a *Borrelia* protein such as the VisE protein. VisE can be applied to the sample pad with or without biotinylated C6 protein. About 3-5 drops of streptavidin-gold and flow buffer are added, and capillary forces pull the liquid to over test lines and towards the wick at the end. The lines give either a positive or negative result, depending whether *Borrelia* (or the synthetic protein) is present. In some embodiments, the QuickLyme test has research applications, including surveying of the number of infected ticks in a certain area.

In one embodiment, the test procedure can proceed following the steps outlined below:
1. Gather materials and safety equipment including nitrile gloves
2. Cut Nitrocellulose into 0.5 cm strips from 10 cm×10 cm sheets and lay on microscope slides
3. Cut pads of glass fiber and cellulose into small rectangles
4. Dilute solutions
5. Carefully apply 3 μl of antibody and 3 μl of biotin albumin in two separate lines using pipette across cellulose strip, then let air dry
   For a negative test (no *Borrelia* protein/VisE), apply 20 μl total of flow buffer containing 3 μl of C-6 peptide and 3 μl of coloring solution (streptavidin-gold)
   For a positive test (mimicking *Borrelia* bacteria presence), apply 3 μl of VisE protein in addition to 3 μl of C6 peptide and 3 μl of coloring solution (streptavidin-gold)
6. Apply 500 μl of flow buffer to sample pad area after applying reagents for both positive and negative test strips.

In one embodiment, the nitrocellulose strip is pre-wet with flow buffer to facilitate moving of the sample in the direction of flow.

Figure 3:
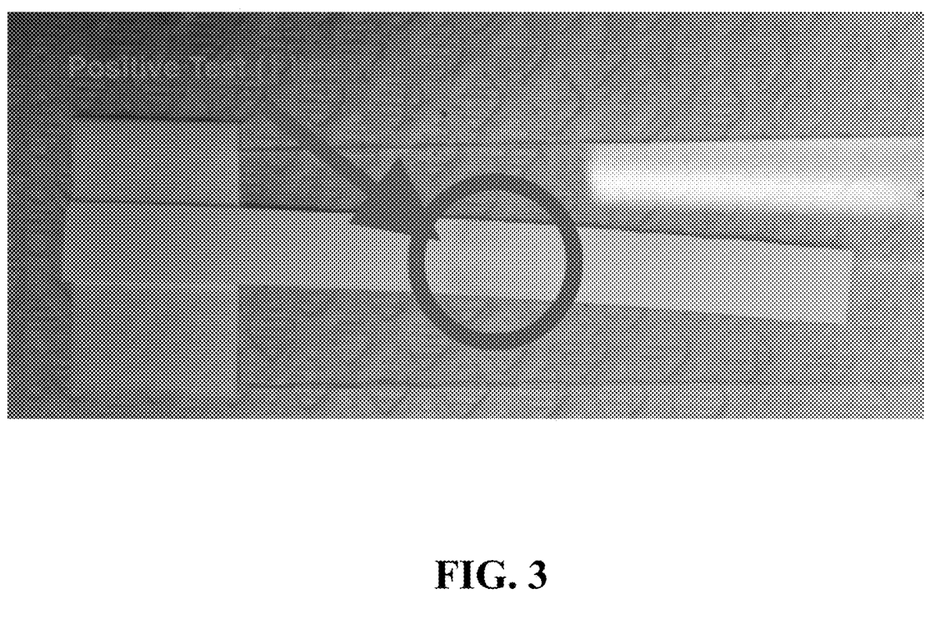
FIG. 3 shows a positive test for the presence *Borrelia burgdorferi*.
Figure 4:
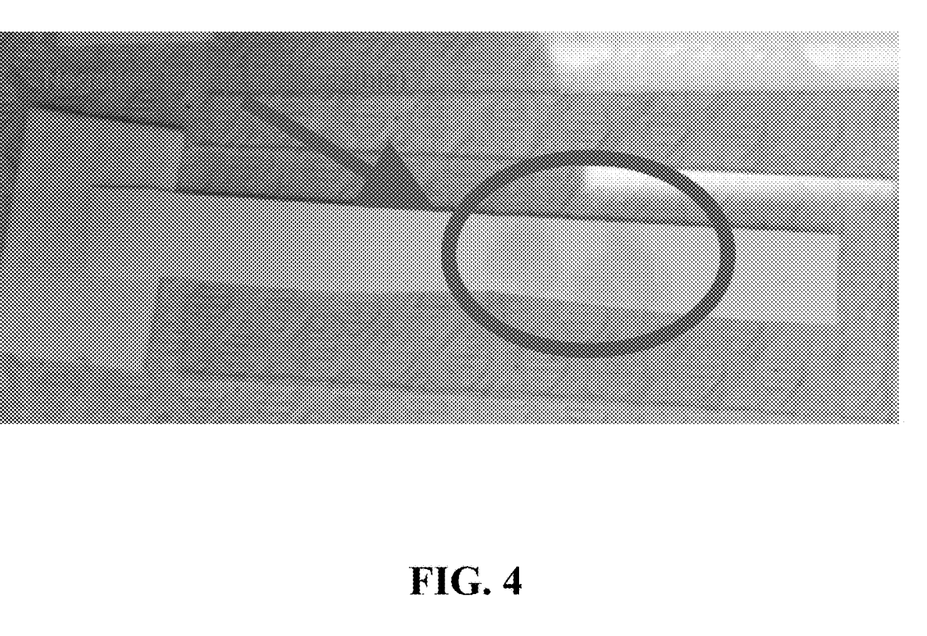
FIG. 4 shows a negative test for the presence *Borrelia burgdorferi*.

As shown in FIG. 3, a positive QuickLyme test for VisE protein results in visualization of one red read-out line, which is the control line. As shown in FIG. 4, a negative test QuickLyme for VisE results in visualization of two red read-out lines.

Materials and Methods
VisE protein (VisE Proteip Rockland Immunochemicals, Inc., Limerick, Pa.)
VisE-Peptide-biotin (Met-Lys-Lys-Asp-Asp-Gln-Ile-Ala-Ala-Ala-Ile-Ala-Leu-Arg-Gly-Met-Ala-Lys-Asp-Gly-Lys-Phe-Ala-Val-Lys-biotinamidocaproyl (SEQ ID NO: 1)—GenScript, Piscataway, N.J.)
VisE antibody (rabbit anti-VisE—Rockland Immunochemicals, Inc., Limerick, Pa.)
Biotin-Albumin (bovine albumin, biotinamidocaproyl-labelled—Sigma Aldrich, Atlanta, Ga.)
Streptavidin-Gold (from *Streptomyces avidinii*, 20 nm particle size—Sigma Aldrich, Atlanta, Ga.)
Phosphate buffered saline (PBS) pH 7.4 (sodium phosphate/NaPO4 50 mM, sodium chloride/NaCl 100 mM), (SigmaAldrich, Atlanta, Ga.)
Tween-20 (Polyoxyethylene-20-sorbitane monolaurate—FisherScientific, Pittsburgh, Pa.)
Nitrocellulose blotting membrane (Amersham Protran Premium 0.45 um NC—GE Healthcare Life Sciences/Amersham, Pittsburgh, Pa.)
Cellulose Fiber Pads (EMD Millipore Corporation, Burlington, Mass.)
Glass Fiber Conjugate Pads (EMD Millipore Corporation, Burlington, Mass.)
Microscope Glass Slides 1"×3"×1 mm (FisherScientific, Pittsburgh, Pa.)
Single Channel Pipets, 10 ul, 20 ul, 200 ul, 1000 ul (Rainin, Woburn, Mass.)
Polyethylene pipet tips, single use, 10 ul, 20 ul, 2000 ul, 1000 ul (Rainin, Woburn, Mass.)
Microcentrifuge tubes, 1.5 ml (Sigma Aldrich, Atlanta, Ga.)
Sterile deionized water (Sigma Aldrich, Atlanta, Ga.)
3D printer (Makerbot Replicator 2, Makerbot Industries, Brooklyn, N.Y.)
PLA-Filament, 1.75 mm (Polylactic acid resin, Makerbot Industries, Brooklyn, N.Y.)
Sketchup Software (Trimble Inc., Sunnyvale, Calif.)
MacBook Pro/OS X 10.12 (Apple Inc., Cupertino, Calif.)

Example 2

Figure 5:
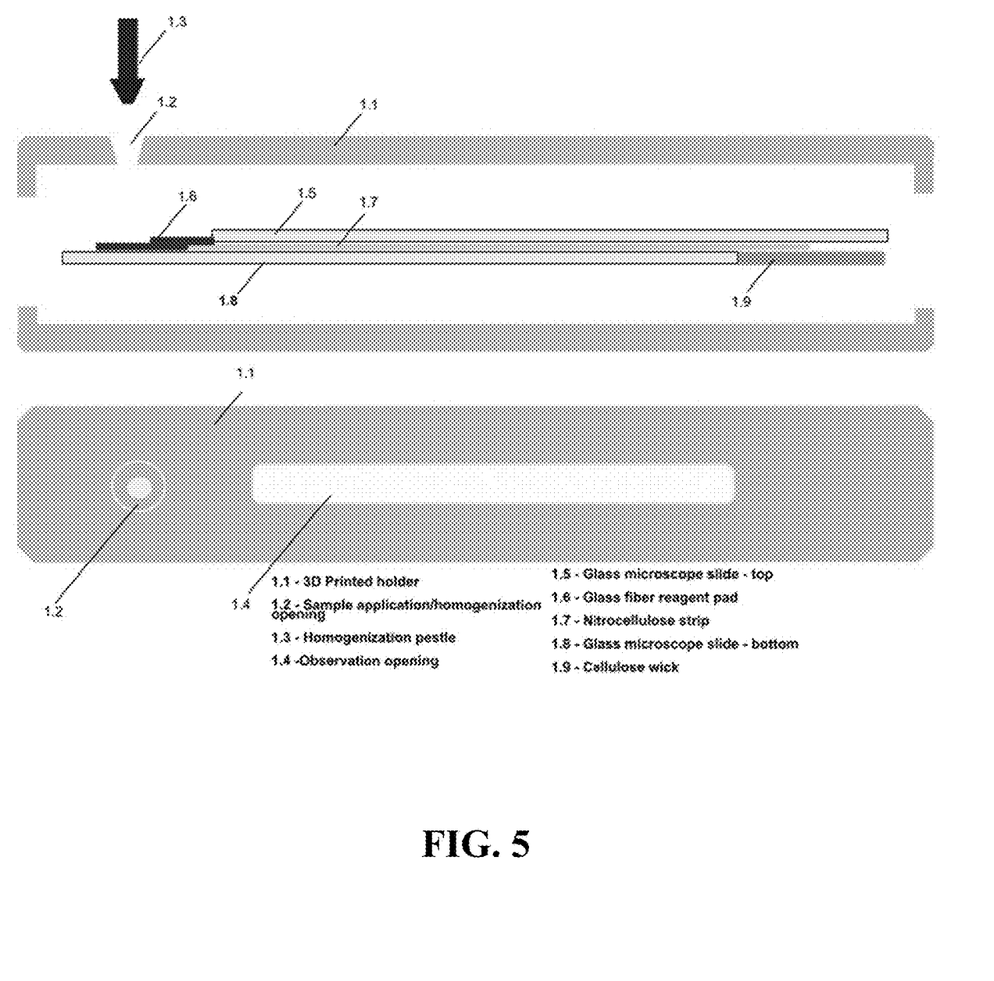
FIG. 5 shows a diagram of a QuickLyme device for detection of *Borrelia burgdorferi*.

The subject matter disclosed herein relates to a QuickLyme device for Lyme disease testing as shown in FIG. 5. In one embodiment, the QuickLyme device can be manufactured following the steps outlined herein. Using Sketchup software package on a Macbook Pro under OS X 12.12, a holder (1.1) for the QuickLyme device is designed. On a Makerbot Replicator 2, both the top and bottom part of the holder (1.1) are printed using Makerbot PLA filament with the PLA standard printing temperature and a layer resolution of 100 microns. In another embodiment, any three-dimensional design software and printer known in the art can be used to manufacture a QuickLyme device. Top (1.5) and bottom (1.8) clear standard microscope glass slides are dip-cleaned in 90% isopropyl alcohol, air dried and positioned between the top and bottom part of the holder (1.1). Using a razor blade, strips of nitrocellulose (10 mm×80 mm) are cut and at least one piece of nitrocellulose strip (1.7) is disposed between the top (1.5) and bottom (1.8) glass slides. Using a razor blade, glass fiber sample/reagent pads (10 mm×10 mm) are cut and at least one piece of sample pad (1.6) is disposed on top of the bottom glass slide (1.8) such that it is not covered by the top glass slide (1.5). Cellulose fiber wicks are cut to 1.5×2.5 cm size and at least one cellulose wick (1.9) is placed under the nitrocellulose strip (1.7) such that it is not covered by the bottom class slide (1.8).

Onto the nitrocellulose strip (1.7), 5 µl of a 1:100 dilution of VisE antibody in PBS are applied in a vertical line at 4 cm from the origin; at 5 cm from a distal end of the sample pad (1.6), 5 µl of biotin-albumin (1 mg/ml in PBS) are applied in a vertical line as well. The nitrocellulose strip is air dried for 30 minutes. Onto one edge of the glass fiber sample pad (1.6), 5 µl of biotinylated C6 peptide solution in PBS are applied and air dried as well. In one embodiment, the holder (1.1) can be assembled as shown in FIG. 5. A clean microscope slide (1.8) is placed in the bottom part of the 3D-printed holder (1.1), a nitrocellulose strip (1.7) with VisE antibody and biotin-albumin is laid on top as indicated in FIG. 5. A glass fiber sample pad (1.6) containing peptide is placed at one end and a cellulose fiber wick (1.9) is placed on the opposite end of the nitrocellulose strip (1.7). The strip assembly is covered with a clean microscope slide as indicated (1.5), overlapping the cellulose wick (1.9) and leaving the sample pad (1.6) accessible. The top part of the 3D-printed holder is placed ensuring that a sample opening (1.2) is directly over the glass fiber sample pad (1.6) and the nitrocellulose strip (1.7) visible through an observation opening (1.4) as shown in FIG. 5.

During testing, sample can be applied onto the sample opening (1.2). When a tick is placed in the sample opening (1.2), the pestle (1.3) is used to manually homogenize the tick onto the sample pad before applying flow buffer. In one embodiment, the sample may contain more than one tick. About 0.5 ml of phosphate-buffered saline with about 0.5% tween, pH 7.4 are added followed by about 0.75 ml of streptavidin-gold conjugate in the same buffer. In one embodiment, the sample buffer can be applied on the one or more homogenized ticks to facilitate movement of tick-associated proteins through the nitrocellulose strip via capillary action.

Through the observation opening, the nitrocellulose strip (1.7) can be monitored for color development of the test and control lines which can occur within 2-3 minutes. A strip showing two red lines indicates the absence of Borrelia proteins from a sample. A strip showing only one red line indicates the presence or Borrelia proteins in a sample.

Materials
Makerbot 2 3D Printer+ software
Glass fiber Pads
Cellulose Pads
Borrelia (Vise-synthetic/non-harmful)
Borrelia antibody (anti-vise)
C6-Peptide
Coloring Solution (SAV-Gold)
Microscope Slides
Pipettes
Flow Buffer (Phosphate Buffered Saline can keep pH stable)

REFERENCES

1. "Lyme Disease." Centers for Disease Control and Prevention, 19 Jan. 2018,
2. Wong, Raphael C., and Harley Y. Tse. Lateral flow immunoassay. Springer, 2010.
3. https://www.cdc.gov/ticks/tickbornediseases/Tickborne-Diseases-P.pdf
4. https://www.who.int/news-room/fact-sheets/detail/vector-borne-diseases

What is claimed is:

1. A method for detecting *Borrelia burgdorferi* bacteria in a sample, the method comprising:
   homogenizing a sample on a sample pad using a pestle;
   applying biotinylated C6 peptide, streptavidin-gold, and flow buffer to the homogenized sample to obtain a homogenized sample solution;
   allowing for capillary flow of said homogenized sample solution to occur along an elongated nitrocellulose strip contacting said sample pad at a first short edge;
   allowing the homogenized sample solution to contact a first read-out line on the nitrocellulose strip and a second read-out line on the nitrocellulose strip;
   wherein the first read-out line comprises at least one VisE-specific antibody;
   further wherein the second read-out line comprises biotinylated albumin; and
   collecting excess sample in a cellulose wick contacting a second short edge of said nitrocellulose strip;
   wherein: (1) the first read out line does not change color if bacterial is detected in the sample; or (2) the first read out line changes color if bacteria is not detected in the sample.

* * * * *

SEQUENCE LISTING

<160> NUMBER OF SEQ ID NOS: 1

<210> SEQ ID NO 1
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Met Lys Lys Asp Asp Gln Ile Ala Ala Ala Ile Ala Leu Arg Gly Met
1               5                   10                  15

Ala Lys Asp Gly Lys Phe Ala Val Lys
            20                  25